United States Patent
Lee et al.

(10) Patent No.: US 11,524,328 B2
(45) Date of Patent: Dec. 13, 2022

(54) BRAIDED MEDICAL DEVICES

(71) Applicants: STRYKER CORPORATION, Kalamazoo, MI (US); STRYKER EUROPEAN OPERATIONS LIMITED, Carrigtwohill (IE)

(72) Inventors: Andrew S. Lee, San Jose, CA (US); Mark Phung, Union City, CA (US); Hancun Chen, San Ramon, CA (US); Timothy Odell, Fremont, CA (US)

(73) Assignee: Stryker Corporation, Kalamazoo, MI (US)

( * ) Notice: Subject to any disclaimer, the term of this patent is extended or adjusted under 35 U.S.C. 154(b) by 127 days.

(21) Appl. No.: 16/824,295

(22) Filed: Mar. 19, 2020

(65) Prior Publication Data
US 2020/0215599 A1    Jul. 9, 2020

Related U.S. Application Data

(63) Continuation of application No. 15/617,883, filed on Jun. 8, 2017, now abandoned.
(Continued)

(51) Int. Cl.
*A61B 17/12*    (2006.01)
*B21F 45/00*    (2006.01)
(Continued)

(52) U.S. Cl.
CPC ...... *B21F 45/008* (2013.01); *A61B 17/12113* (2013.01); *A61B 17/12163* (2013.01);
(Continued)

(58) Field of Classification Search
CPC ........ A61B 17/12022; A61B 17/12027; A61B 17/12031; A61B 17/12036;
(Continued)

(56) References Cited

U.S. PATENT DOCUMENTS 5,423,849 A * 6/1995 Engelson ......... A61B 17/12022
                                                           604/907
6,217,609 B1    4/2001 Haverkost et al.
(Continued)

FOREIGN PATENT DOCUMENTS

WO    WO 95/09586    4/1995
WO    WO 97/16133    5/1997
(Continued)

OTHER PUBLICATIONS

PCT International Search Report and Written Opinion for International Application No. PCT/US2017/036602, Applicant Stryker Corporation, dated Jan. 2, 2018 (23 pages).
(Continued)

*Primary Examiner* — Darwin P Erezo
*Assistant Examiner* — Christian D Knauss
(74) *Attorney, Agent, or Firm* — Vista IP Law Group, LLP

(57) ABSTRACT

A braided vaso-occlusive member formed out of first plurality of filaments interwoven with a second plurality of filaments, wherein filaments of the first plurality are helically wound in a first rotational direction along an elongate axis of the braided member, and filaments of the second plurality are wound in a second rotational direction opposite the first rotational direction, such that filaments of the first plurality cross over and/or under filaments of the second plurality at each of a plurality cross-over locations axially spaced along the elongate axis of the braided member, wherein at each cross-over location, the filaments of the first plurality cross over at least two consecutive filaments of the second plurality, then cross under only a single filament of the second plurality, and then cross over at least two additional consecutive filaments of the second plurality.

11 Claims, 11 Drawing Sheets

Related U.S. Application Data

(60) Provisional application No. 62/348,659, filed on Jun. 10, 2016.

(51) Int. Cl.
| | | |
|---|---|---|
| *A61F 2/90* | (2013.01) | |
| *D04C 1/06* | (2006.01) | |
| *A61B 17/00* | (2006.01) | |
| *A61B 90/00* | (2016.01) | |
| *A61F 2/82* | (2013.01) | |
| *A61F 2/88* | (2006.01) | |

(52) U.S. Cl.
CPC .. *A61B 17/12172* (2013.01); *A61B 17/12177* (2013.01); *A61F 2/90* (2013.01); *D04C 1/06* (2013.01); *A61B 2017/00526* (2013.01); *A61B 2090/392* (2016.02); *A61F 2/885* (2013.01); *A61F 2002/823* (2013.01); *A61F 2250/0017* (2013.01); *A61F 2250/0039* (2013.01); *A61F 2250/0098* (2013.01); *D10B 2403/0333* (2013.01); *D10B 2509/06* (2013.01)

(58) Field of Classification Search
CPC .......... A61B 17/1204; A61B 17/12109; A61B 17/12113; A61B 17/12118; A61B 17/1214; A61B 17/12145; A61B 17/1215; A61B 17/12163; A61B 17/12168; A61B 17/12172; A61B 17/12177; A61B 17/221; A61B 2017/2212; A61B 2017/2215; A61B 2017/2217; A61F 2/90; A61F 2002/823; A61F 2/88; A61F 2/885; A61F 2/013; A61F 2/014; A61F 2002/015; A61F 2002/016

See application file for complete search history.

(56) References Cited

U.S. PATENT DOCUMENTS

| | | | |
|---|---|---|---|
| 6,547,820 | B1 | 4/2003 | Staudenmeier |
| 8,715,314 | B1 | 5/2014 | Janardhan et al. |
| 9,011,482 | B2 | 4/2015 | Wallace et al. |
| 9,060,777 | B1 | 6/2015 | Wallace et al. |
| 2003/0069629 | A1 | 4/2003 | Jadhav |
| 2011/0130819 | A1 | 6/2011 | Cragg |
| 2012/0168022 | A1 | 7/2012 | Rasmussen et al. |
| 2015/0313605 | A1* | 11/2015 | Griffin ............ A61B 17/12172 606/200 |
| 2015/0374483 | A1* | 12/2015 | Janardhan ............... A61M 1/74 606/200 |
| 2016/0249935 | A1* | 9/2016 | Hewitt ............ A61B 17/12031 606/200 |

FOREIGN PATENT DOCUMENTS

| | | |
|---|---|---|
| WO | WO 2008/112242 | 9/2008 |
| WO | WO 2009/135166 | 11/2009 |
| WO | WO 2010/139340 | 12/2010 |
| WO | WO 2012/112749 | 8/2012 |
| WO | WO 2014/105932 | 7/2014 |
| WO | WO 2017/139702 | 8/2017 |

OTHER PUBLICATIONS

PCT Invitation to Pay Additional Fees for International Application No. PCT/US2017/036602, Applicant Stryker Corporation, dated Oct. 6, 2017 (18 pages).

Comprehensive Study of Textile from Fiber to Fashion editor Mazharul Islam Kiron, article downloaded from http://textilelearner.blogspot.com/2016/06/study-textile-fiber-fashion.html?sm_au_=iWBtSLIZWHZNLQP, accessed and printed on Jun. 5, 2017, 10 pages.

* cited by examiner

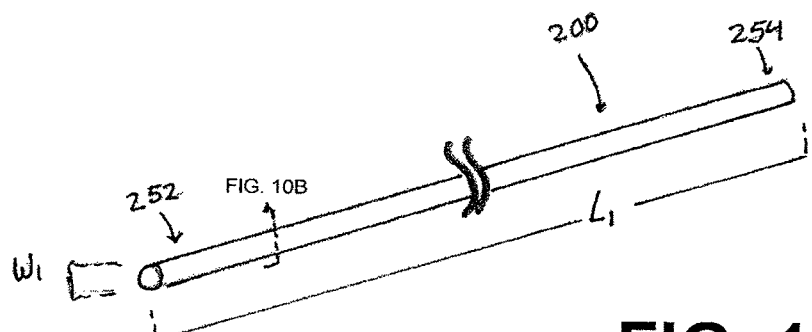
FIG. 10A
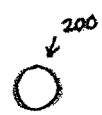
FIG. 10 B
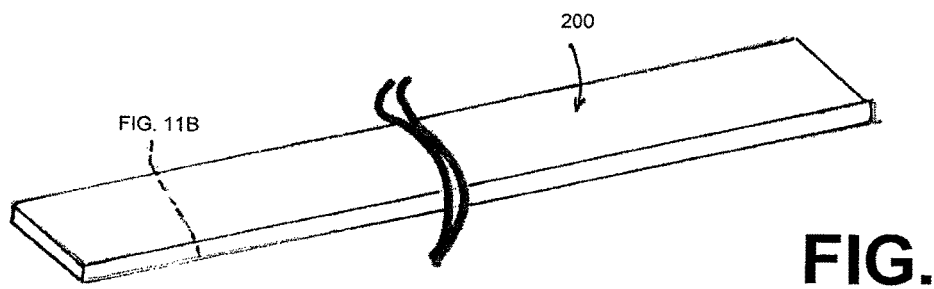
FIG. 11A
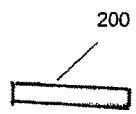 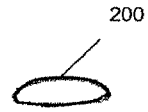 
FIG. 11B   FIG. 12A   FIG. 12B

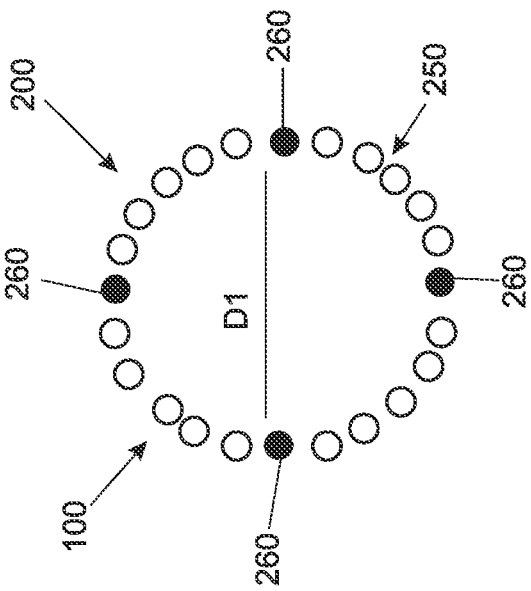
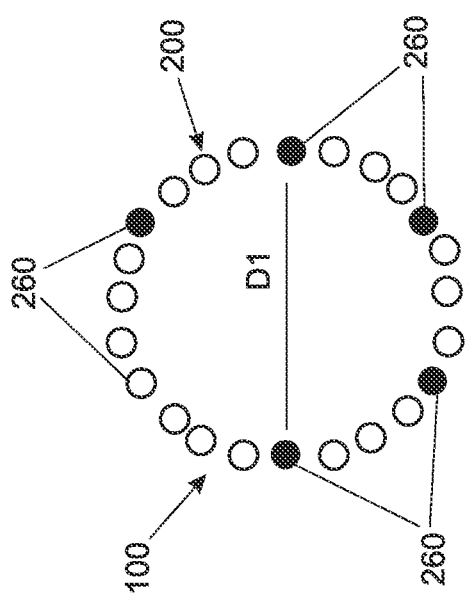
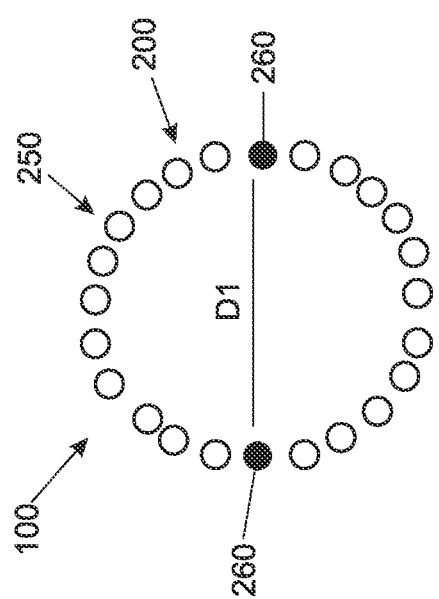
FIG. 14
FIG. 15
FIG. 13

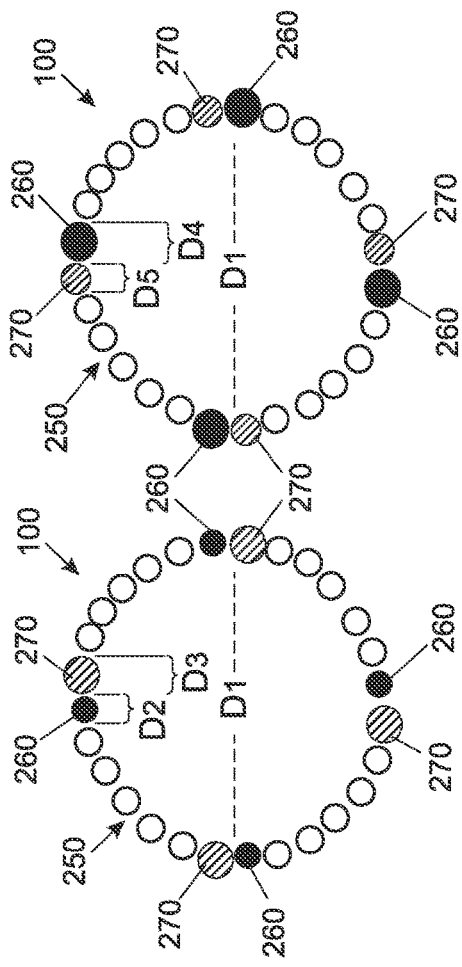
FIG. 16
FIG. 17A
FIG. 17B
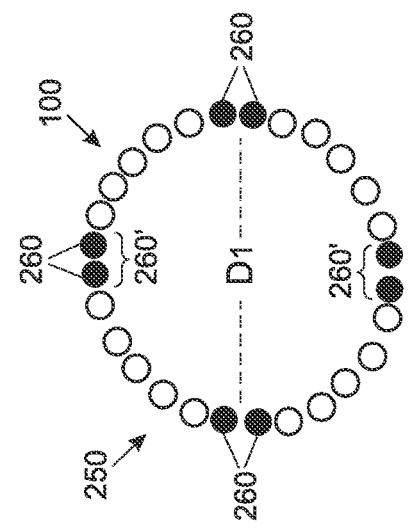
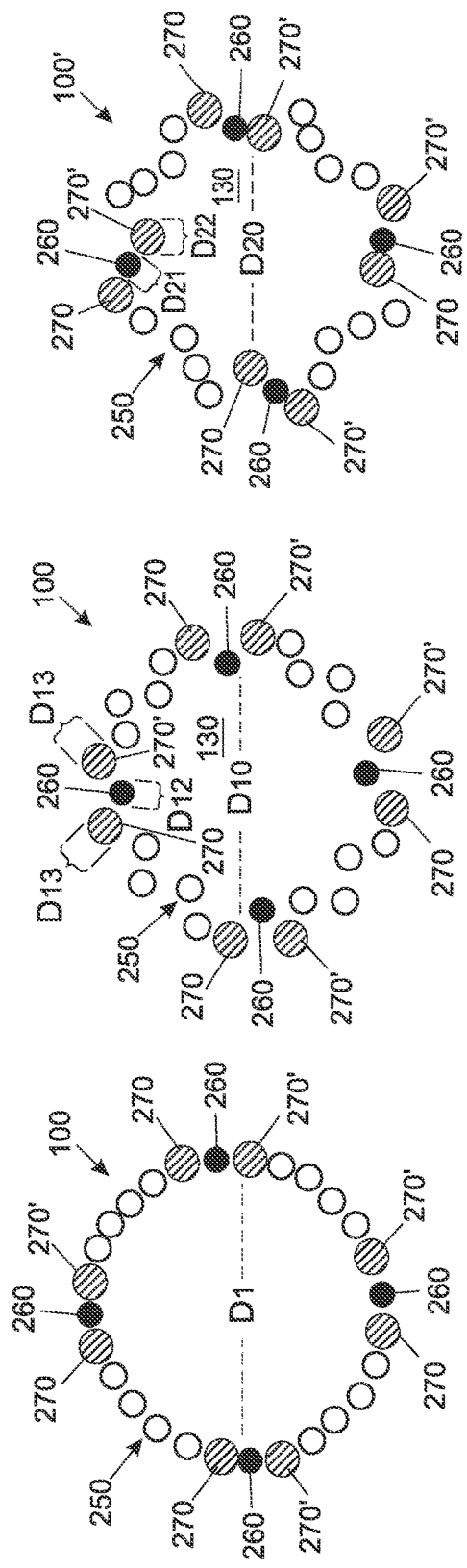
FIG. 18
FIG. 19
FIG. 20

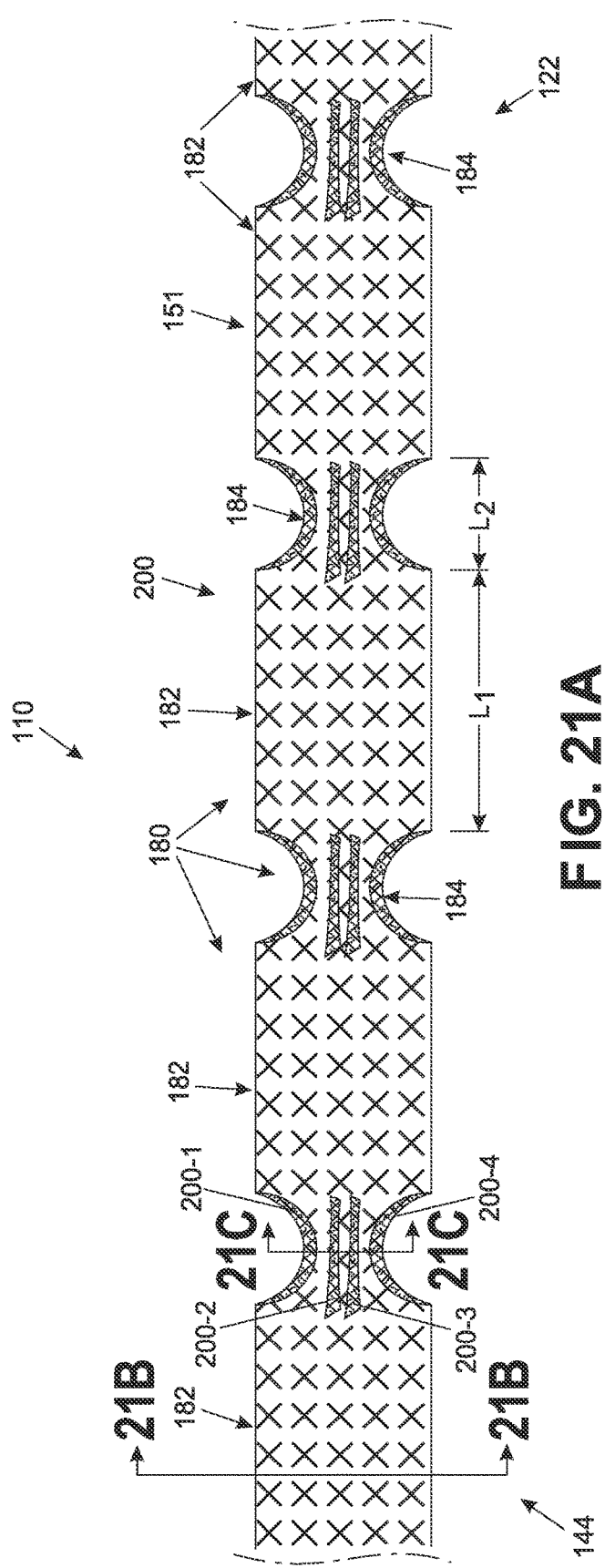
FIG. 21A
FIG. 21B
FIG. 21C
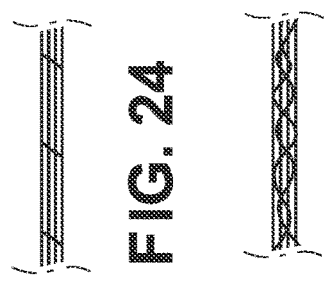
FIG. 24
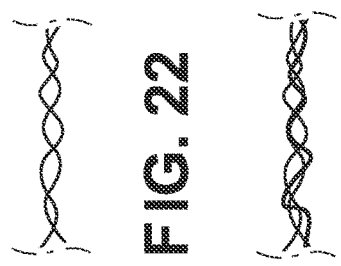
FIG. 25
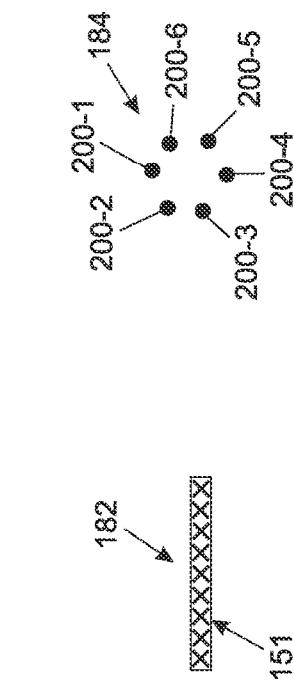
FIG. 22
FIG. 23

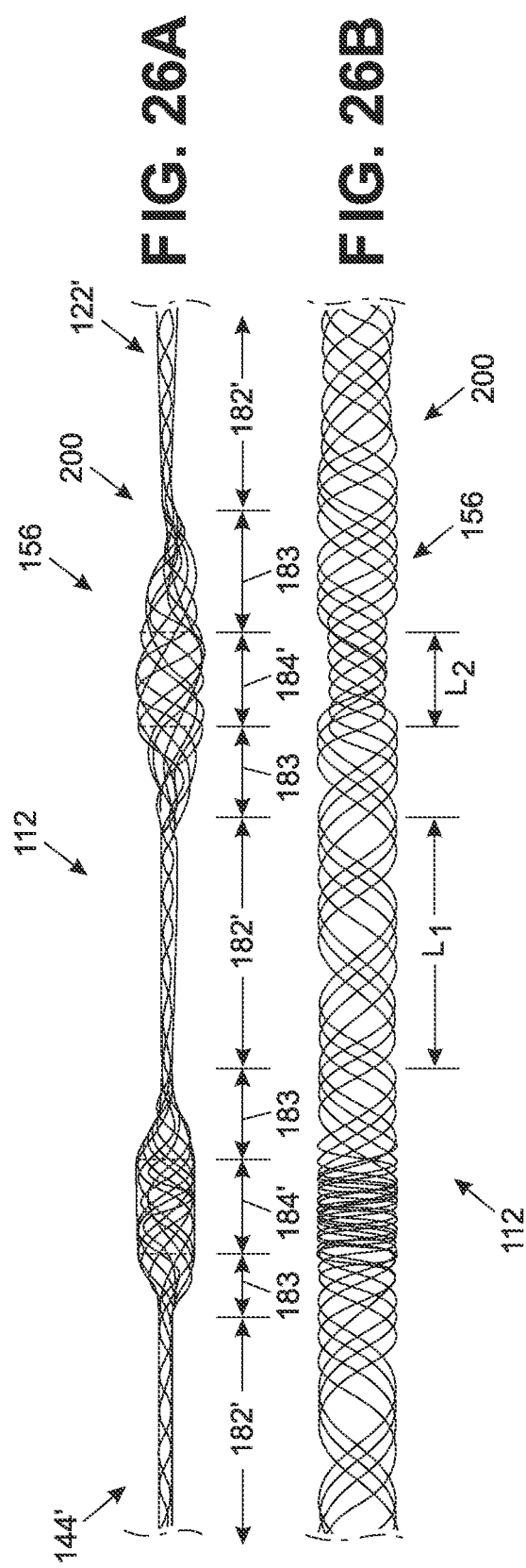

11,524,328 B2

BRAIDED MEDICAL DEVICES

RELATED APPLICATION DATA

This patent application is a continuation of U.S. patent application Ser. No. 15/617,883, filed on Jun. 8, 2017, which claims the benefit under 35 U.S.C. § 119 to U.S. Provisional Application Ser. No. 62/348,659, filed Jun. 10, 2016. The foregoing applications are hereby incorporated by reference into the present application in its entirety.

FIELD

The inventions disclosed herein relate to braided medical devices used for the treatment of vascular defects, such as aneurysms, and more particularly to woven braid patterns to be used in such braided medical devices.

BACKGROUND

Medical devices such as stents, filters, thromboembolic capture devices, flow diverters, vaso-occlusive devices, collectively referred to herein as "embolic devices" are often composed of one or more elongate members (e.g., wires, drawn-filled tubes, threads, filaments and the like) that are woven into a braid or mesh pattern. Such braided embolic devices may be utilized for treating various types of vascular defects, such as aneurysms, and may be provided in a wide variety of respective delivery and deployed sizes and shapes; particularly, secondary shapes when the device is deployed in a targeted vasculature site. Some exemplary secondary shapes of braided embolic devices include spherical, ovoid, flat ribbon, helical braided ribbon, or combinations thereof, suitable for the treatment of vascular defects.

Braided embolic devices are commonly made out of self-expanding materials, so that when the devices are deployed from a delivery system into the target site in a patient, the unconstrained devices expand without requiring assistance. Self-expanding embolic devices may be biased so as to cause the braided device to expand upon release from a delivery catheter and/or include a shape-memory component, which allows the device to expand upon exposure to a predetermined condition (e.g., in-vivo conditions). Some embolic devices may be characterized as hybrid devices which have some characteristics of both self-expandable materials and non-self-expandable materials.

Additionally, the respective elongate members (wires, drawn-filled tubes, threads, filaments and the like) forming the braid may be made from a variety of materials, including both bio-erodible and non-bio-erodible polymers and metals. In some applications, bio-erodible polymer embolic devices are desirable due to their biodegradability and generally increased flexibility compared to metal embolic devices. Further, embolic devices can be made from shape memory or superelastic materials, such as shape memory metals, e.g., Nitinol, and polymers, e.g., polyurethane. Such shape memory embolic devices can be induced by known shape setting techniques, e.g., temperature, electrical, magnetic field and/or exposure to narrowband light to take on a secondary shape after delivery within a targeted vascular site. Superelastic embolic materials, such as superelastic Nitinol, may take on a shape after delivery without need for an inductive stimulus. Other materials used in the embolic devices can include stainless steel, titanium, platinum, nickel, chrome cobalt alloy, Elgiloy, or the like, and combinations thereof. In drug delivery embolic devices, the device can carry and/or the surface of the device can be coated with a bioactive or therapeutic agent, e.g., thrombosis inducing agent.

In the treatment of vascular defects, such as aneurysms, the braided embolic device is typically loaded into (or onto) a delivery system in a collapsed or radially compressed delivery configuration. The delivery system—typically a so-called micro-catheter—is percutaneously introduced in a patient, generally by so called minimally invasive techniques. The braided embolic device is then distally advanced through the delivery system and introduced into a targeted vasculature site of the patient. As such the braided embolic device must have a suitable "pushability" that allows the translation of the device through the lumen of a delivery catheter. Further, in the treatment of certain vascular defects, the expanded configuration or secondary shape of the braided embolic device should be suitable to engage an embolic obstruction and/or the walls of a blood vessel without overcoming the resistive forces of the vessel.

Particularly, the radial expansion forces of the braided embolic device should be suitable to engage the desired obstructions and/or the blood vessel walls, while being sufficiently flexible (e.g., soft) to avoid damaging the blood vessel at the target site. Therefore, the braided embolic device should have sufficient column strength in the collapsed or radially compressed delivery configuration, allowing the braided embolic devices to be pushed and translated through the delivery system into the target site without buckling, deforming or crumpling. Additionally, a suitable combination of stiffness and flexibility in the braided embolic device is desirable, for the device to be pulled, re-sheathed, or to pull an engaged obstruction from the vessel, while being sufficiently flexible when delivered into the target site.

Some braided embolic devices achieve a desired flexibility by reducing the diameter or cross-sectional area of the elongate members (i.e., wires) forming the braid or by reducing the amount of elongate members in the braid. However, reducing the diameter of the wires in already low wire diameter limits for embolic devices is challenging to manufacture, and along with reducing the number of wires, these options tend to sacrifice on the needed stiffness of the device. Moreover, these options may negatively impact on the overall performance of the braided embolic device by either reducing the width of the device or decreasing the wire density required to effectively treat a vascular defect. Other braided embolic devices achieve a desired stiffness by having the wires of the braided device welded, bonded or otherwise engaged to each other at a certain angle, which in turn may sacrifice the needed flexibility of the device. Techniques addressing the above delivery and deployment concerns for braided embolic devices are described in U.S. Pat. Nos. 9,011,482 and 9,060,777, the entire disclosures of which are incorporated herein by reference, as though set forth in full.

FIGS. 1A-B illustrate an exemplary prior art braided embolic device in the form of a tubular braided stent 10. FIG. 1A shows the braided stent 10 in a radially expanded delivered configuration, having a proximal portion 12, a distal portion 14 and a lumen 16 extending therebetween. The braided stent 10 is formed out of a plurality of elongate members (e.g., wires, drawn-filled tubes, threads, filaments and the like) 20 that are woven together. FIG. 1B is a two-dimensional plan view of a section of a wall 18 of the braided stent 10, showing that the elongate braid members 20 are woven in a standard repeating "one-over, one-under" pattern 50, which is a common weave pattern used in known braided embolic devices. In the one-over, one-under braid pattern, each braid member of a first set of elongate braid members 22 cross over and under each braid member of a second set of braid members in an alternating manner, wherein the elongate braid members of the first set are substantially orthogonal to the elongate braid members of the second set (and vice versa). Similarly, the elongate braid members 24 of the second set each extend over/under the respective braid members of the first set 22 in the same alternating one-over, one-under pattern, "over" and "under" being relative terms that depend on which facing side of the wall section 18 is being viewed. The repeating one-over, one-under braid pattern provides the stent 10 with sufficient column strength in the radially compressed delivery configuration allowing the embolic devices to be pushed and translated through the delivery system. However, this standard braid pattern also reduces the flexibility and softness of the stent 10 when deployed at a target site in the vasculature.

SUMMARY

In an exemplary embodiment of one of the disclosed inventions, an implantable vaso-occlusive device is provided for occluding an aneurysm, the device comprising a braided member formed out of a first plurality of filaments interwoven with a second plurality of filaments, the braided member having a compressed configuration when constrained in a lumen of a delivery catheter, and an expanded configuration when not constrained. The braided member filaments of the first plurality are helically wound in a first rotational direction along an elongate axis of the braided member, and filaments of the second plurality are wound in a second rotational direction opposite the first rotational direction along the elongate axis of the braided member, such that filaments of the first plurality cross over and/or under filaments of the second plurality at each of a plurality cross-over locations axially spaced along the elongate axis of the braided member, wherein at each cross-over location, the filaments of the first plurality cross over at least two consecutive filaments of the second plurality, then cross under only a single filament of the second plurality, and then cross over at least two additional consecutive filaments of the second plurality.

Without limitation, at each cross-over location, the filaments of the first plurality may be oriented substantially orthogonal to the filaments of the second plurality when the device is in an expanded, non-constrained configuration. Also, without limitation, the first rotational direction may be clockwise, and the second rotational direction may be counter-clockwise.

In one embodiment, at each cross-over location, the filaments of the first plurality cross over exactly two consecutive filaments of the second plurality, then cross under only a single filament of the second plurality, and then cross over exactly two more consecutive filaments of the second plurality. In other embodiments, at each cross-over location, the filaments of the first plurality cross over at least three consecutive filaments of the second plurality, then cross under only a single filament of the second plurality, and then cross over at least three more consecutive filaments of the second plurality. By way of a non-limiting example, a braided device according to one embodiment may comprise a first body portion and a second body portion, and at each cross-over location in the first body portion, the filaments of the first plurality cross over two or three consecutive filaments of the second plurality, then cross under only a single filament of the second plurality, and then cross over at least two or three more consecutive filaments of the second plurality.

In an exemplary embodiment of another one of the disclosed inventions, an implantable vaso-occlusive device is provided for occluding an aneurysm, the device comprising a braided member formed out of braid filaments, the braided member having an compressed configuration when constrained in a lumen of a delivery catheter, and a tubular expanded configuration when not constrained, wherein when the braid member is in the expanded configuration, the braid filaments are disposed circumferentially about an elongate axis of the braided member. The braid filaments comprising a plurality of filaments made out of a first material, and one or more marker filaments made of a second material having a higher stiffness and a higher radiopacity, respectively, than the first material filaments.

By way of non-limiting examples, the vaso-occlusive device first material filaments may be made out of nickel-titanium alloy, and the marker filaments may be made out of platinum alloy. In one embodiment, the marker filaments include first and second marker filaments that are circumferentially offset approximately 180° from each other along at least a portion of the braided device when the braided device is in the tubular expanded configuration, wherein the first marker filament is made out of a different material and/or has a different diameter, respectively, than the second marker filament. In another embodiment, the marker filaments include four marker filaments that are circumferentially offset approximately 90° from each other along at least a portion of the braided device when the braided device is in the tubular expanded configuration, wherein at least one of the four marker filaments is made out of a different material and/or has a different diameter, respectively, than at least one other of the four marker filaments. In yet another embodiment, the marker filaments include six marker filaments that are be circumferentially offset approximately 60° from each other along at least a portion of the braided device when the braided device is in the tubular expanded configuration, wherein at least one of the six marker filaments is made out of a different material and/or has a different diameter, respectively, than at least one other of the six marker filaments.

In various exemplary embodiments, the marker filaments of the vaso-occlusive device include a first set of adjacent maker elements and a second set of adjacent marker elements, wherein the first set of adjacent marker elements may be circumferentially offset approximately 180° from the second set of adjacent marker elements along at least a portion of the braided device when the braided device is in the tubular expanded configuration. The first set of adjacent marker filaments comprising first and second marker filaments disposed adjacent one another, wherein the first marker filament is made out of a different material and/or has a different diameter, respectively, than the second marker filament.

Without limitation, the first marker filament may be made out of platinum alloy, and the second marker filament may be made out of nitinol and platinum drawn-filled tube. In one embodiment, the first set of adjacent marker filaments include first, second and third marker filaments disposed adjacent each other, wherein first marker filament is made out of a different material and/or has a different diameter, respectively, than one or both of the second and third marker filaments.

In an exemplary embodiment of yet another one of the disclosed inventions, an implantable vaso-occlusive device is provided for occluding an aneurysm, the device comprising a braided member formed out of a plurality of interwoven braid filaments, the braided member having an compressed configuration when constrained in a lumen of a delivery catheter, and an expanded configuration when not constrained, in which the braid filaments are disposed circumferentially about an elongate axis of the braided member, wherein in the expanded configuration, the braided member defines a plurality of segments having enlarged cross-sections (referred to herein as "enlarged cross-section segments") spaced apart along the elongate axis thereof, wherein adjacent enlarged cross-section segments of the plurality are connected by a respective reduced cross-section segment, and wherein the braid filaments are interwoven according to a first weave pattern to create the respective enlarged cross-section segments, and wherein the braid filaments are interwoven according to a second weave pattern different than the first weave pattern to create each reduced cross-section segments.

By way of non-limiting example, in the second weave pattern, subsets of the plurality of interwoven braid filaments are wound into respective linking braids and/or wire bundles that span between adjacent enlarged cross-section segments. In the expanded configuration of the vaso-occlusive device, a respective reduced cross-section segment may be outwardly expanded into a fattened, ribbon-like configuration about the elongate axis, and the enlarged cross-section segments may be circumferentially expanded about the elongate axis.

Other and further aspects and features of embodiments will become apparent from the ensuing detailed description in view of the accompanying figures.

BRIEF DESCRIPTION OF THE DRAWINGS

FIGS. 10A and 10B are respective perspective and cross-sectional views of an exemplary elongate braid member that may be used for constructing braided embolic devices, such as the device of FIGS. 8-9.

FIGS. 11A and 11B are respective perspective and cross-sectional views of an alternate exemplary elongate braid member that may be used for constructing braided embolic devices, such as the device of FIGS. 8-9.

FIGS. 12A and 12B are respective cross-sectional views of an alternate exemplary elongate braid member that may be used for constructing braided embolic devices, such as the device of FIGS. 8-9.

FIGS. 13-20 are cross-sectional views of exemplary braided embolic devices, constructed according to embodiments of the disclosed inventions.

FIGS. 21A-C are perspective and cross-sectional views of another exemplary braided embolic devices, constructed according to embodiments of the disclosed inventions.

FIGS. 22-25 are perspective views of exemplary elongate sets of plurality of elongate members, constructed according to embodiments of the disclosed inventions.

FIGS. 26A-B are perspective side and top views of yet another exemplary braided embolic devices, constructed according to embodiments of the disclosed inventions

DETAILED DESCRIPTION OF THE ILLUSTRATED EMBODIMENTS

Figure 1A:
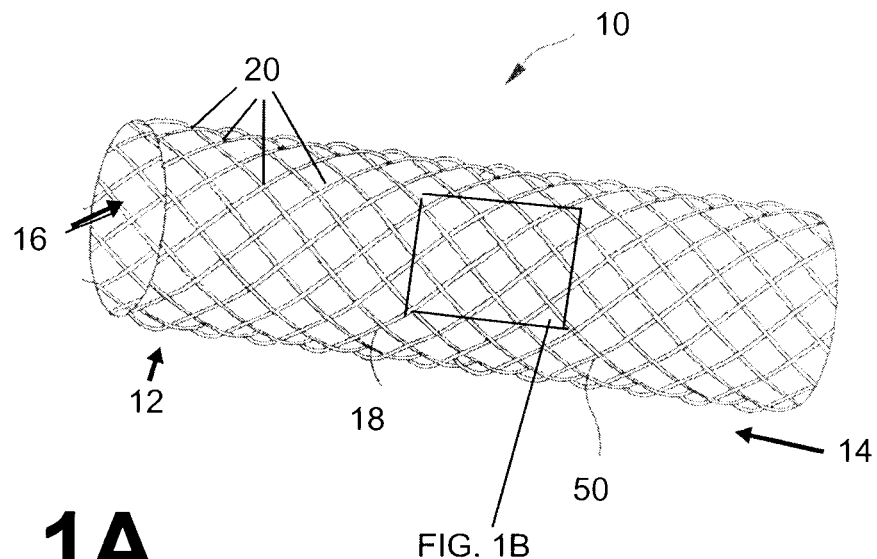
FIGS. 1A and 1B are respective perspective and plan side views of a Prior Art braided embolic device having a standard repeating "one-over, one-under" braid pattern.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

As used in this specification and the appended claims, the singular forms "a", "an" and "the" include plural referents unless the content clearly dictates otherwise. As used in this specification and the appended claims, the term "or" is generally employed in its sense including "and/or" unless the content clearly dictates otherwise.

Figure 2:
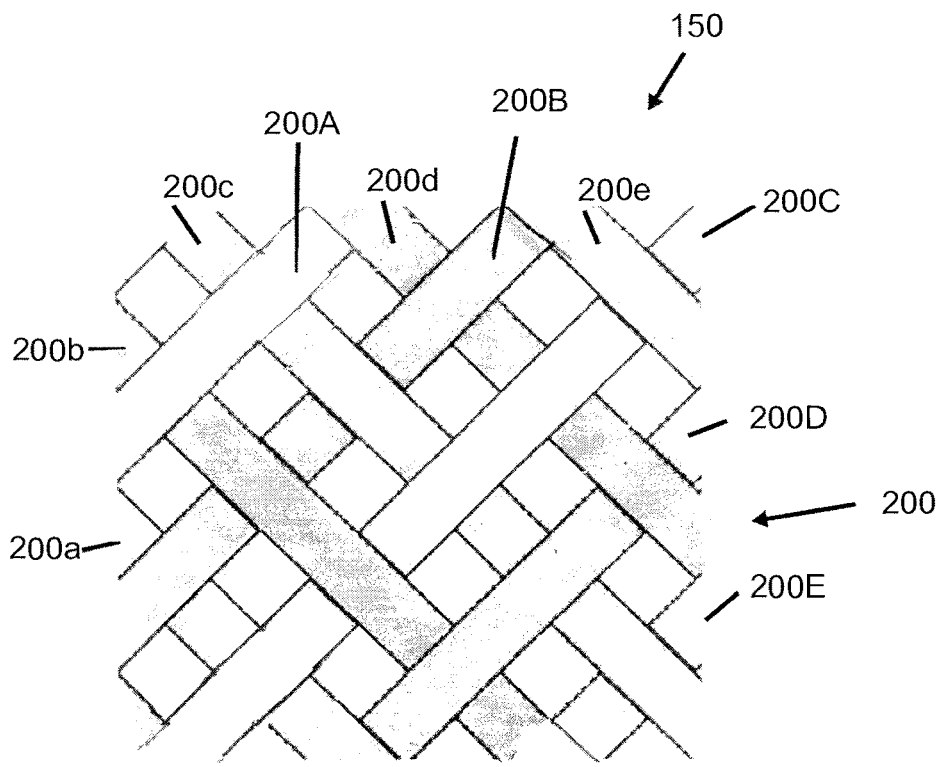
FIG. 2 is a plan view of a repeating "two-over, one-under" braid pattern that may be used for constructing braided embolic devices, according to one embodiment of the disclosed inventions.

FIG. 2 illustrates a two-dimensional plan view of an exemplary braid 150 that may be used for constructing a braided embolic device, according to one embodiment of the disclosed inventions. The braid 150 is formed by a plurality of inter-woven elongate members 200, including a first set of elongate members 200A-E inter-woven with a second set of elongate members 200a-e, wherein the elongate members 200A-E are substantially orthogonally disposed with respect to the elongate members 200a-e. In particular, the elongate members 200A-E and 200a-e are interwoven in a repeating "two-over, one under" pattern, wherein each elongate member of each set 200A-E and 200a-e extends over two successive elongate members, and then under the next successive elongate member, respectively, of the other set.

For example, when viewed from the perspective shown in FIG. 2 (e.g., one/front side of the braid 150), the elongate member 200A of the first set extends over successive elongate members 200b and 200c, then under the elongate member 200d, respectively, of the second set. Similarly, when viewed from the opposite side of the braid 150 that is depicted in FIG. 2, the elongate member 200c of the second set extends over successive elongate members 200C and 200D, then under the next elongate member 200E, respectively, of the first set.

Figure 3:
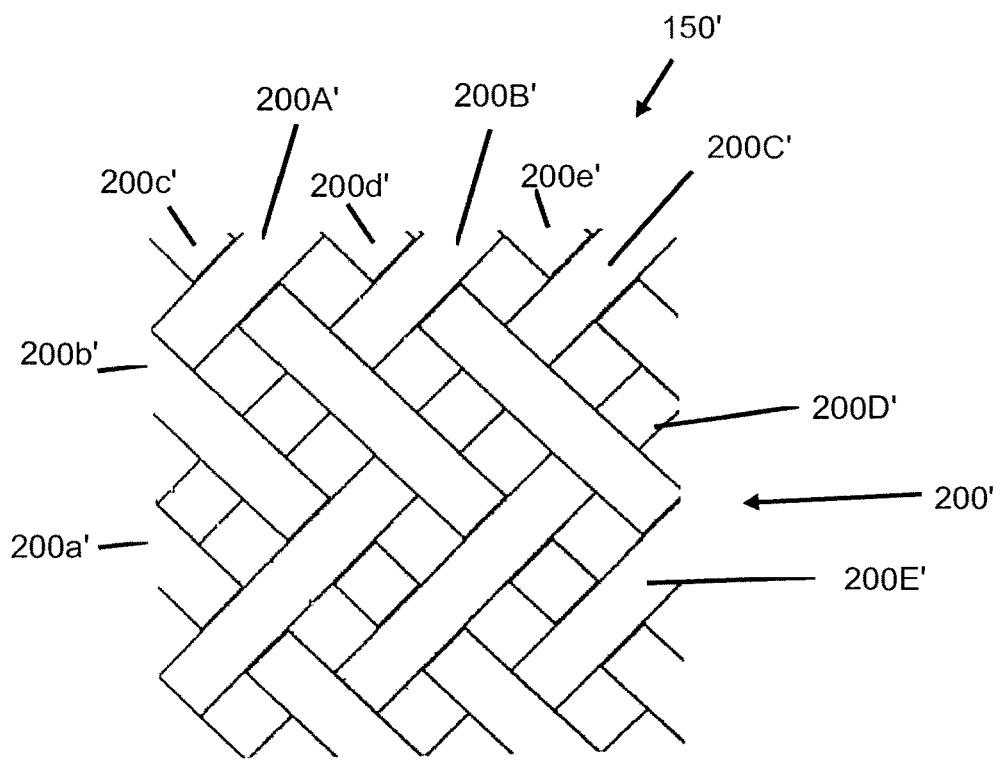
FIG. 3 is a plan view of a repeating "two-over, two-under" braid pattern that may be used for constructing braided embolic devices, according to another embodiment of the disclosed inventions.

FIG. 3 illustrates a two-dimensional plan view of an exemplary braid 150' that may be used for constructing a braided embolic device, according to another embodiment of the disclosed inventions. The braid 150' is formed by a plurality of inter-woven elongate members 200', including a first set of elongate members 200A'-E' inter-woven with a second set of elongate members 200a'-e', wherein the elongate members 200A'-E' are substantially orthogonally disposed with respect to the elongate members 200a'-e'. As depicted in FIG. 3, the elongate members 200A'-E' and 200a'-e' are interwoven in a repeating "two-over, two under" pattern, wherein each elongate member of each set 200A'-E' and 200a'-e' extends over two successive elongate members, and then under the next two successive elongate members, respectively, of the other set. For example, when viewed from the perspective shown in FIG. 3 (e.g., one/front side of the braid 150'), the elongate member 200C' of the first set extends over successive elongate members 200a' and 200b', then under the elongate members 200c' and 200d' of the second set. Similarly, when viewed from the opposite side of the braid 150' that is depicted in FIG. 3, the elongate member 200c' of the second set extends over successive elongate members 200D' and 200E', then under elongate members 200B' and 200C' of the first set.

Figure 4A:
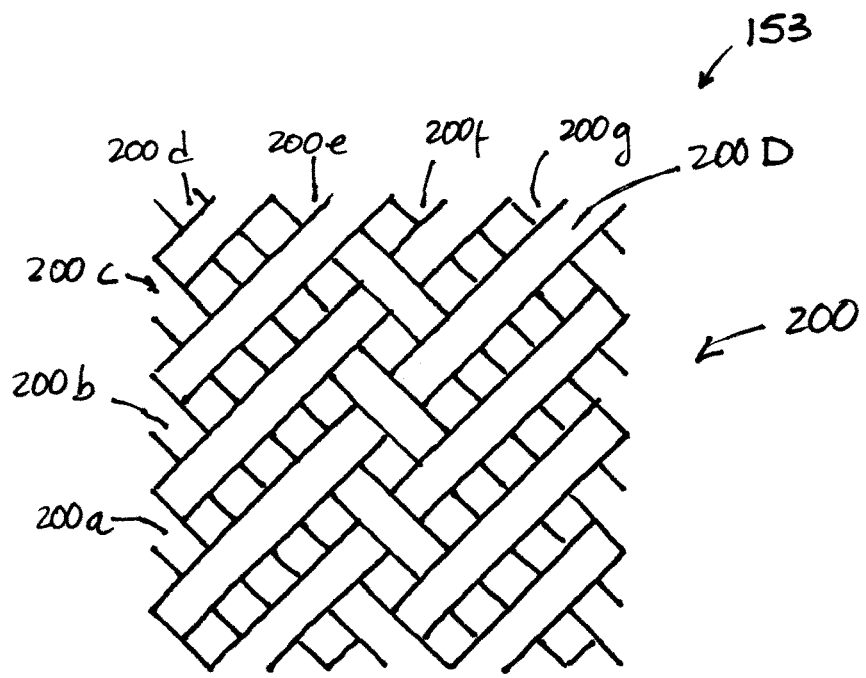
FIGS. 4A and 4B are respective front and back plan views of a repeating "three-over, one-under" braid pattern that may be used for constructing braided embolic devices, according to yet another embodiment of the disclosed inventions.
Figure 4B:
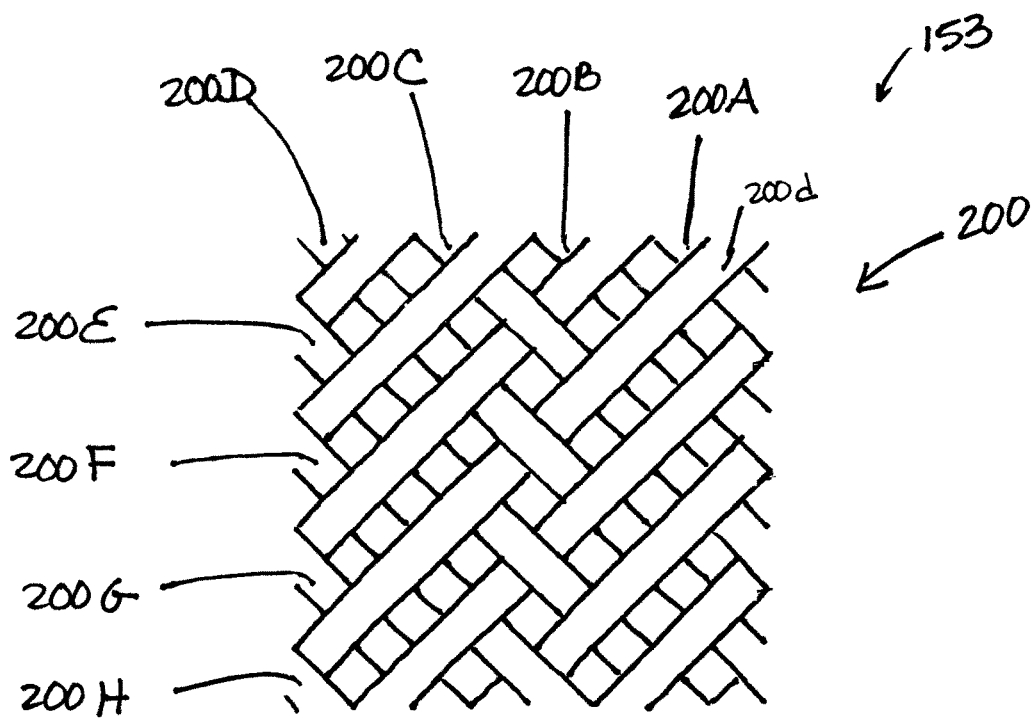

FIGS. 4A and 4B are plan views of an alternative braid 153 that may be used for constructing braided embolic devices according to further embodiments of the disclosed inventions. As was the case of the braid 150 shown in FIG. 2, the braid 153 shown in FIGS. 4A and 4B is formed out of two sets of elongate braid members 200 that are interwoven. But in braid 153, the elongate braid members 200 are interwoven in a repeating "three-over, one-under" pattern. For example, when viewed from the perspective shown in FIG. 4A (e.g., one/front side of the braid 153), the elongate member 200D of the first set extends over successive elongate members 200a, 200b and 200c, then under the elongate member 200d, of the second set. Further, the elongate member 200D of the first set continues to extend over successive elongate members 200e, 200f and 200g (FIG. 4A), then under the elongate member 200h (not shown). Similarly, when viewed from the opposite side of the braid 153 that is depicted in FIG. 4B, the elongate member 200d of the second set extends over successive elongate members 200A, 200B and 200C, then under the next elongate member 200D. Further, the elongate member 200d of the second set continues to extend over successive elongate members 200E, 200F and 200G, then under the elongate member 200H of the first set.

Figure 5:
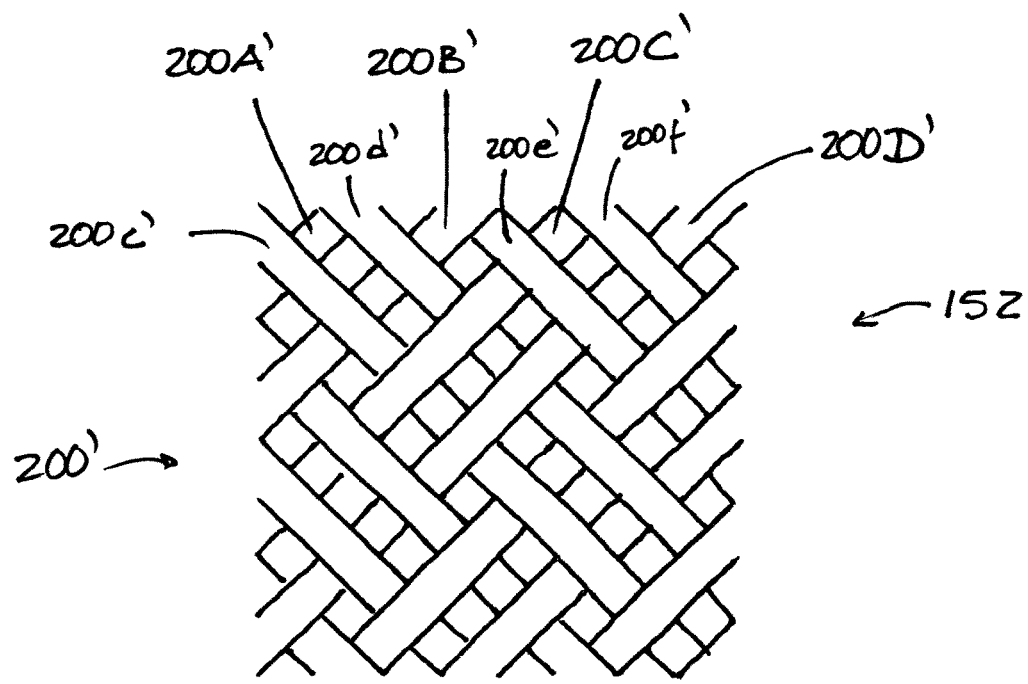
FIG. 5 is a plan view of a repeating "two-over, two-under" braid pattern that may be used for constructing braided embolic devices, according to other embodiment of the disclosed inventions.

FIG. 5 is a plan view of an alternative braid 152 that may be used for constructing braided embolic devices according to further embodiments of the disclosed inventions. As was the case of the braid 150' shown in FIG. 3, the braid 152 shown in FIG. 5 is formed out of two sets of elongate braid members 200' that are interwoven. But in braid 152, the elongate braid members 200 are interwoven in a repeating and adjacently successive "two-over, two-under" pattern. For example, when viewed from the perspective shown in FIG. 5 (e.g., one/front side of the braid 152), both of the adjacently disposed elongate member 200c' and 200d' of the second set extend over successive elongate members 200A' and 200B', then under elongate members 200C' and 200D' of the first set. Similarly, when viewed from the opposite side of the braid 152 that is depicted in FIG. 5, both of the adjacently disposed elongate member 200C' and 200D' of the first set extend over successive elongate members 200e' and 200f, then under the elongate members 200c' and 200d' of the second set.

Figure 6:
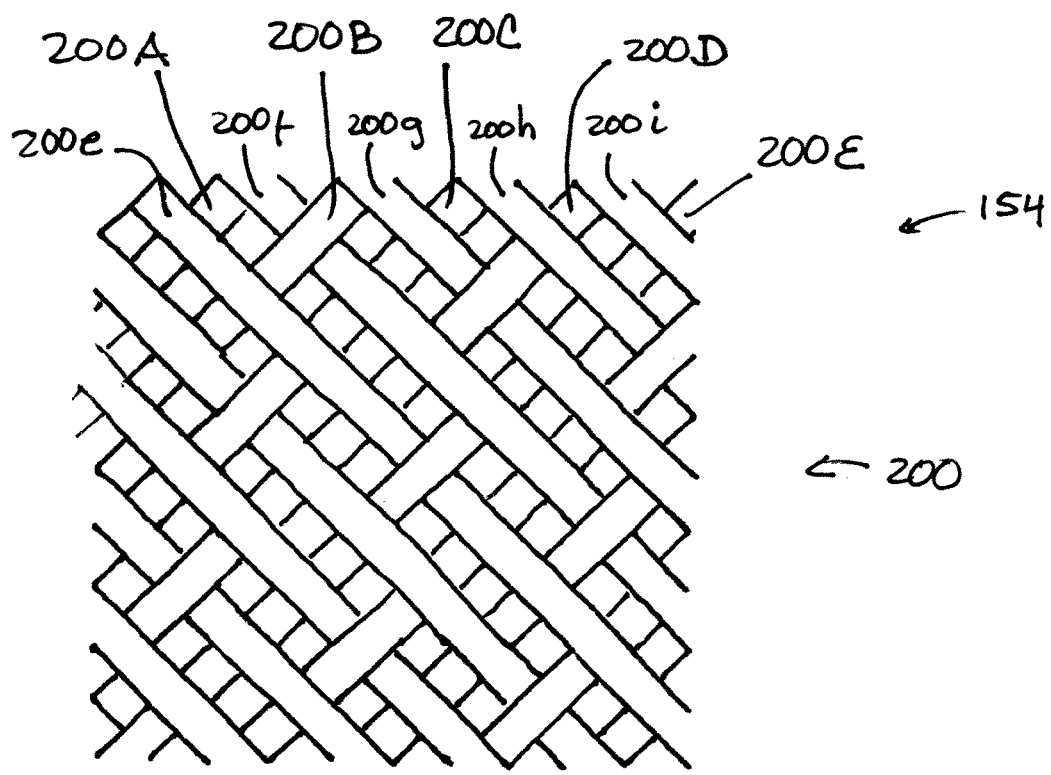
FIG. 6 is a plan view of a repeating "four-over, one-under" braid pattern that may be used for constructing braided embolic devices, according to other embodiment of the disclosed inventions.

FIG. 6 is a plan view of an alternative braid 154 that may be used for constructing braided embolic devices according to further embodiments of the disclosed inventions. As was the case of the braid 150 shown in FIG. 2, the braid 154 shown in FIG. 6 is formed out of two sets of elongate braid members 200 that are interwoven. But in braid 154, the elongate braid members 200 are interwoven in a repeating "four-over, one-under" pattern. For example, the elongate member 200e of the second set extends over successive elongate members 200A, 200B, 200C and 200D, then under the elongate member 200E of the first set. Similarly, when viewed from the opposite side of the braid 154 that is depicted in FIG. 6, the elongate member 200E of the first set extends over successive elongate members 200i, 200h, 200g and 200f, then under the next elongate member 200e of the second set.

Figure 7:
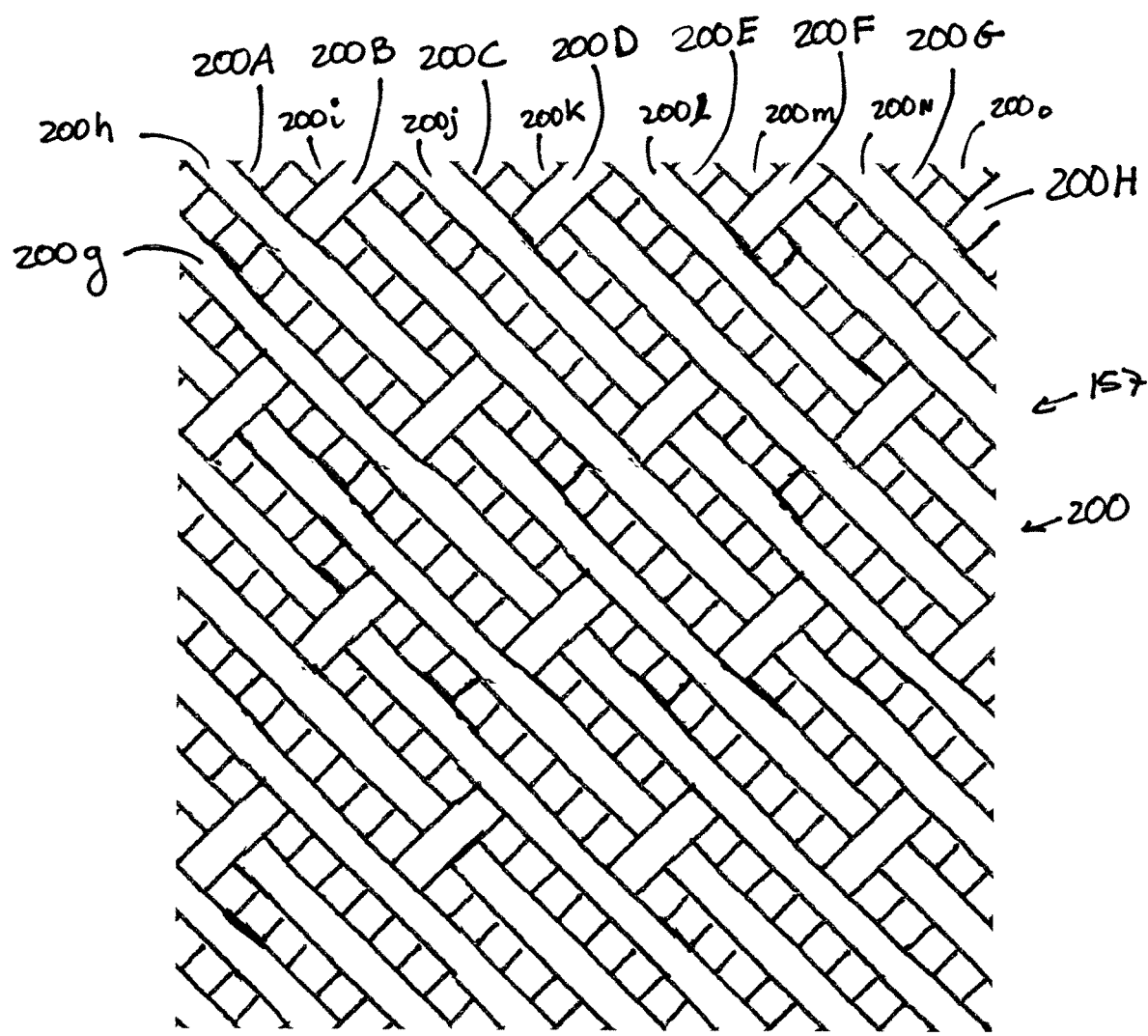
FIG. 7 is a plan view of a repeating "seven-over, one-under" braid pattern that may be used for constructing braided embolic devices, according to other embodiment of the disclosed inventions.

FIG. 7 is a plan view of an alternative braid 157 that may be used for constructing braided embolic devices according to further embodiments of the disclosed inventions. The braid 157 shown in FIG. 7 is formed out of two sets of elongate braid members 200 that are interwoven, similarly to the braid 150 shown in FIG. 2. However in braid 157, the elongate braid members 200 are interwoven in a repeating "seven-over, one-under" pattern. For example, when viewed from the perspective shown in FIG. 7 (e.g., one/front side of the braid 157), the elongate member 200g of the second set extends over successive elongate members 200A, 200B, 200C, 200D, 200E, 200F and 200G, then under the elongate member 200H of the first set. Further, when viewed from the opposite side of the braid 157 that is depicted in FIG. 7, the elongate member 200H of the first set extends over successive elongate members 200o, 200n, 200m, 200l, 200k, 200j and 200i, then under the next elongate member 200h of the second set.

Figure 1B:
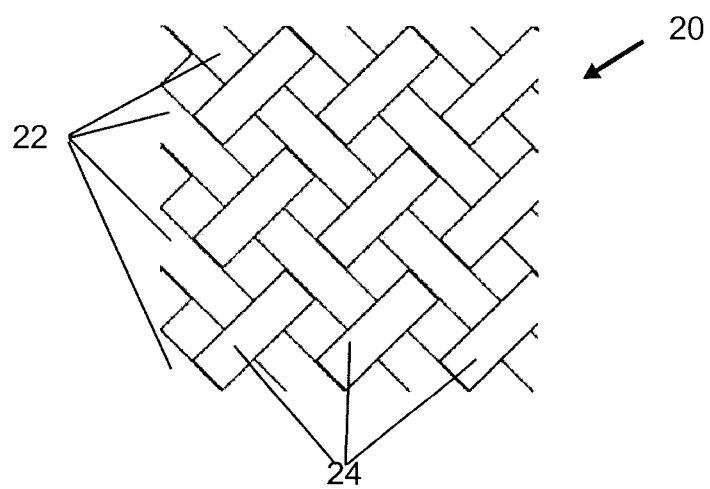

As shown in FIGS. 2-7, the braid for embolic devices may comprise a variety of braid patters. By way of non-limiting and additional examples, the braid patterns may include "five-over, one-under", "six-over, one-under", "eight-over, one-under" patterns, and/or "three-over, three-under", "four-over, four-under" patterns (not shown) or the like or combinations thereof. The disclosed braid patterns or combination thereof incorporated into an embolic device provides the device (e.g., stent) with suitable stiffness (e.g., column strength), particularly, when the embolic device is in a radially compressed delivery configuration within a delivery system, allowing the device to be translated, pushed or moved through the lumen of the delivery system for deployment at a target site. Further, the embolic devices having a braid constructed with the disclosed braid patterns or combination thereof, allows the device to smoothly translate through the delivery system by providing lower surface area in the device which in turn lowers the frictional forces (e.g., resistance) from the delivery system into the embolic device. Moreover, the disclosed braid pattern provides for an increased flexibility and softness in the embolic device, as compared with a braid employing the standard one-over, one-under pattern (e.g., FIGS. 1A-B). The increased flexibility and softness of the embolic device is particularly desirably after the device is deployed at a target site, conforming to the target site in a patient while avoiding injury or damage to the target site. The disclosed braid patterns or combination thereof (e.g., FIGS. 2-7) provide an optimal balance between longitudinal and radial stiffness during delivery, and flexibility after delivery of the embolic device.

Figure 8:
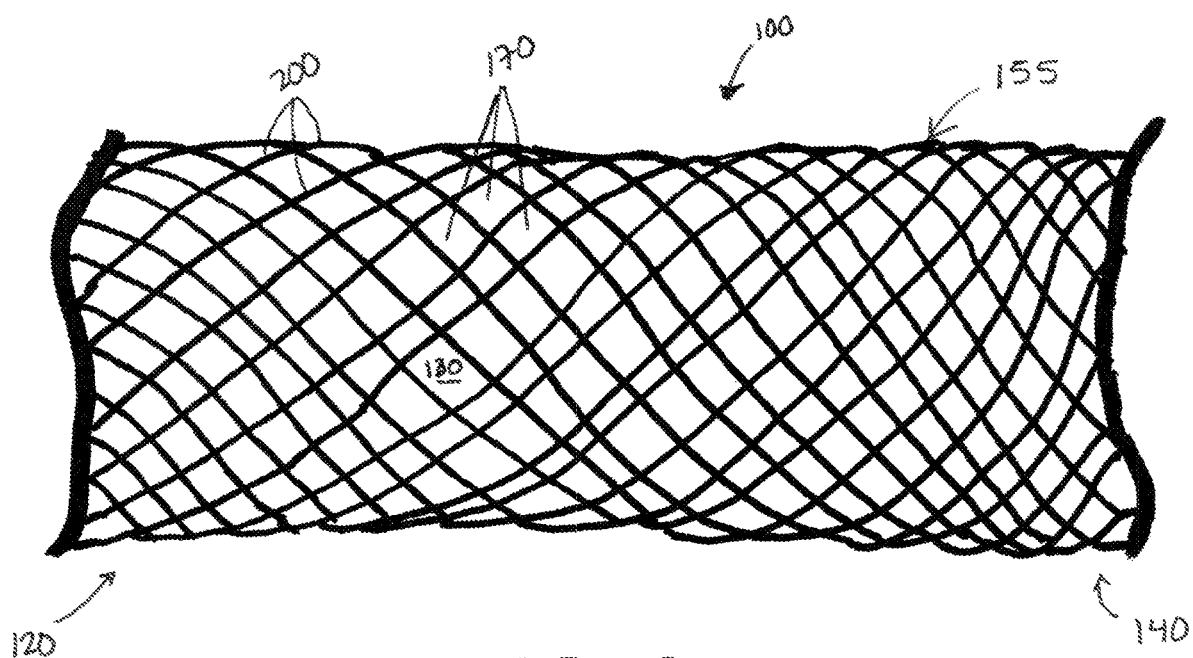
FIG. 8 is a perspective view of an exemplary tubular embolic device having any of the braid patterns of previously disclosed embodiments.

FIG. 8 illustrates an exemplary braided embolic device 100 constructed according to one embodiment of the disclosed inventions, and incorporating one or a combination of the braid patterns of the disclosed inventions, such as in FIGS. 2-7. The braided embolic device 100 comprises a tubular configuration having a distal portion 120, a proximal portion 140 and a lumen 130 extending therebetween. The embolic device 100 has a radially compressed delivery configuration (not shown), and a radially expanded deployed configuration (shown in FIG. 8), and preferably comprises a length that ranges from approximately 2 centimeters up to approximately 40 centimeters in the deployed configuration, and more preferably from approximately 5 centimeters up to approximately 25 centimeters in the deployed configuration. The braided embolic device 100 may comprise anywhere from ten to ninety interwoven elongate members, wherein a first set of elongate braid members 200 are interwoven with a second set of elongate braid members in either of the repeating patterns disclosed or a combination thereof. The embolic device 100 may include a braid 155 having the elongate braid members 200 spaced apart in relatively even manner in the radially expanded deployed configuration, as shown in FIG. 8. The braid 155 elongate members 200 define a plurality of openings or cells 170 of similar dimensions, when the embolic device 100 is in the radially expanded deployed configuration. The braid 155 of the embolic device 100 may be formed by any of the disclosed braid pattern, combinations thereof, and/or having a variety of elongate members 200 (e.g., thickness, materials), that will be described in further detail below.

Figure 9:
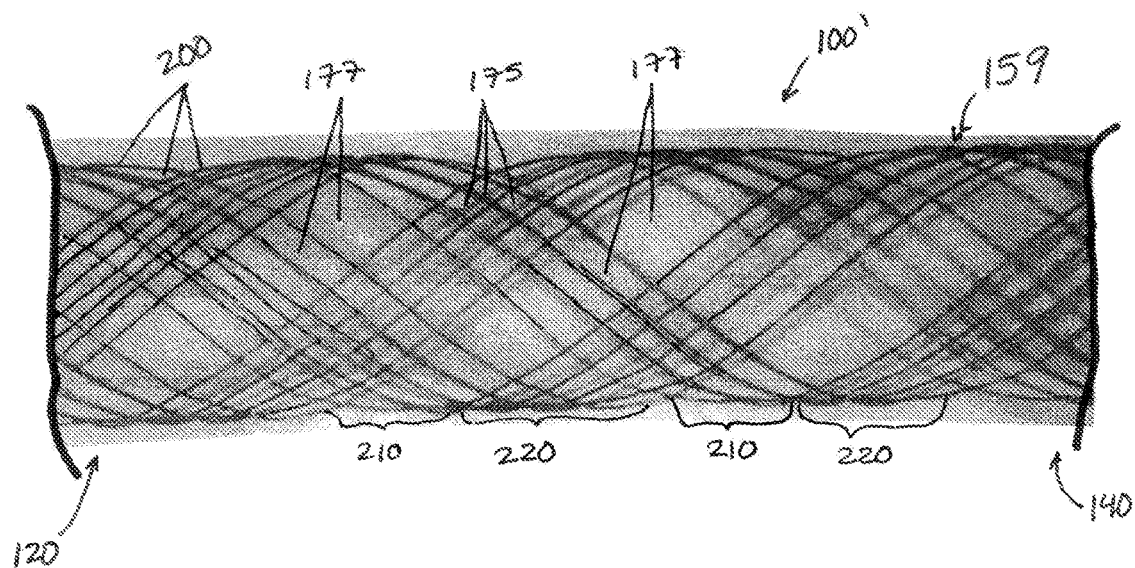
FIG. 9 is a perspective view of an exemplary tubular embolic device having the "two-over, one-under" braid pattern shown in FIG. 2.

FIG. 9 illustrates an exemplary braided embolic device 100' constructed according to another embodiment of the disclosed inventions, and incorporating the repeating "two-over, one under" braid pattern depicted in FIG. 2. The embolic device 100' depicted in FIG. 9 is similar to the embolic device 100 depicted in FIG. 8. One difference is that the embolic device 100' comprises a braid 159 having elongate braid members 200 with a plurality of openings or cells 175 and 177 of different dimensions, when the embolic device 100' is in the radially expanded deployed configuration. For example, the cells 175 have a smaller dimension than the cells 177 of the braid 159. The two-over, one under braid pattern allows the braided embolic device 100' to radially expand into a non-symmetrical deployed configuration, as shown in FIG. 9.

When expanded, the braided embolic device 100' comprises a plurality of sections (or segments) 210 and 220 extending from the proximal portion 120 to the distal portion 140. Each of the sections 210 and 220 comprises a plurality of elongate braid members 200, in which section 210 comprises a less dense arrangement of the elongate braid members 200, in section 220. The repeating "two-over, one-under" pattern still provides suitable stiffness or column strength when the device 100' is in the radially compressed delivery configuration, thereby allowing the device 100' to be pushed through the lumen of a delivery system, while also allowing the device to smoothly translate through the delivery system by providing lower surface area in the device which in turn lowers the frictional forces (resistance) from the delivery system into the embolic device.

It should be appreciated that any of the disclosed braided patterns or a combination thereof, which may have a variety of elongate members forming the braid of the embolic device, may comprise the radially expanded deployed configuration of FIG. 9, or any other suitable expanded configuration. Additionally or alternatively, the radially expanded deployed configuration of the embolic device may comprise evenly-spaced and/or unevenly-spaced elongate members defining a plurality of cells having similar and/or different dimensions, or combinations thereof.

FIGS. 10A and 10B illustrate the elongate member 200 used for constructing braided embolic devices according to embodiments of the disclosed inventions. The elongate member 200 comprises a proximal portion 252 and a distal portion 254, and has a length $L_1$ suitable for achieving a desired braided device length, and a width $W_1$ that preferably is in a range from approximately 0.05 millimeters to approximately 1.00 millimeters, and more preferably in a range from approximately 0.1 millimeters to approximately to 0.4 millimeters. In some embodiments, the width and/or cross-sectional dimensions of the elongate member 200 remain constant along its length. In other embodiments, one or more of the width and/or cross-sectional dimensions of the elongate member 200 vary along its length, e.g., in a tapered configuration (not shown). It should be appreciated that the elongate braid members 200 may have a variable dimensions, such as having a combination of larger and smaller diameter (or cross-section if not round) elongate members in a braid (e.g., braid 150, 150', 152, 153, 154, 155, 157 and 159).

As shown in FIG. 10B, the elongate member 200 comprises a substantially circular cross-section. Alternatively, the elongate member 200 may have any other suitable cross-sections, such as, by way of non-limiting examples, ovoid or elliptical (shown in FIG. 12A), or the elongate member 200 may comprise a ribbon-like configuration having a substantially rectangular cross-section (shown in FIGS. 11A and 11B), or other suitable cross-section, such as, flattened with rounded edges (shown in FIG. 12B), or combinations thereof. Each elongate braid member 200, or portions thereof, may be coated or otherwise formed with a layer of radiopaque material. Additionally, the elongate braid members 200 may carry and/or be coated with a bioactive or therapeutic agent (e.g., thrombosis inducing agent). Additionally or alternatively, each of the elongated braid member 200 may comprise a wire, drawn-filled-tube, threads, filaments or the like, composed by one or more suitable biocompatible materials.

The elongate braid members 200 may be composed from any number of biocompatible, compressible, elastic materials or combinations thereof, including polymeric materials, metals, and metal alloys, such as stainless steel, tantalum, or a nickel titanium alloy such as a super-elastic nickel titanium alloy known as Nitinol. Certain super-elastic alloys may be desirable for their shape recoverable features, which tolerate significant flexing without deformation even when used for forming relatively small elongate braid members. Further when a braided embolic device comprises elongate braid members composed of self-expanding materials, the unconstrained embolic device can be made to be biased to expand into a predetermined deployed configuration, as shown with devices 100 or 100' of FIGS. 8-9. Some super-elastic alloys that may be useful for this purpose include nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum).

Further suitable metals and alloys for the elongate braid members include "platinum group" metals, such as, platinum, rhodium, palladium, rhenium, as well as tungsten, gold, silver, tantalum, and alloys of these metals, such as platinum/tungsten alloy, or the like and combinations thereof. These metals have significant radiopacity and in their alloys may be tailored to accomplish an appropriate blend of flexibility and stiffness. Moreover, a variety of different imaging methods can be used to ensure accurate positioning of the braided embolic devices within a delivery system and when deployed in a patient. Examples of suitable imaging methods include biplane fluoroscopy, digital subtraction angiography with road mapping technology, venous angiography with road mapping technology, and the like. The embolic devices may comprise radio-opaque materials or markers that allow viewing of the position of the device under fluoroscopy.

FIGS. 13-16 illustrate cross-sectional views of braided embolic devices comprising radiolucent and radio-opaque members, according to the embodiments of the disclosed inventions. The braided embolic devices 100 of FIGS. 13-16 comprise radiolucent members 250 composed of stainless steel, Nitinol, biocompatible polymers or other suitable materials. As shown in FIG. 13, the braided embolic device 100 comprises two evenly-spaced radio-opaque members 260 (cross-sectional views of elongate members 200) along the diameter $D_1$ of the device 100. Alternatively, the braided embolic device 100 of FIG. 14 comprises four evenly-spaced radio-opaque members 260 along the diameter $D_1$, and FIG. 15 comprises six evenly-spaced radio-opaque members 260 along the diameter $D_1$. The braided embolic device 100 of FIG. 16 comprises four sets 260' of evenly-spaced radio-opaque members along the diameter $D_1$, where each set 260' comprises two adjacently disposed radio-opaque members 260. The radio-opaque members 260 comprise filaments composed of platinum. It should be appreciated that other radio-opaque materials may be used in members 260.

In alternative embodiments, FIGS. 17A-B comprise four evenly-spaced radio-opaque members 260 along the diameter $D_1$ composed of platinum and four evenly-spaced radio-opaque members 270 along the diameter $D_1$ composed of Nitinol, where each of the members 260 are adjacently disposed to a respective member 270. The members 260 and 270 may comprise different diameters. By way of non-limiting example, the members 260 have a smaller diameter $D_2$ than the diameter $D_3$ of members 270 in FIG. 17A; conversely, the members 260 have a larger diameter $D_4$ than the diameter $D_5$ of members 270 in FIG. 17B.

In another alternative embodiment, FIG. 18 comprises four evenly-spaced radio-opaque members 260 along the diameter $D_1$ composed of platinum, a first set of four evenly-spaced radio-opaque members 270 along the diameter $D_1$, and a second set of four evenly-spaced radio-opaque members 270' along the diameter $D_1$. The members 270 and 270' are composed of Nitinol. As shown in FIG. 18, each of the members 260 is disposed between respective members 270 and 270', the members 260 have a smaller diameter $D_6$ than the diameter $D_7$ of members 270 and 270'.

In yet another alternative embodiment, FIG. 19 comprises four evenly-spaced radio-opaque members 260 along the diameter $D_{10}$ composed of platinum, a first set of four evenly-spaced radio-opaque members 270 along the diameter $D_{10}$, and a second set of four evenly-spaced radio-opaque members 270' along the diameter $D_{10}$. The members 270 and 270' are composed of Nitinol. As shown in FIG. 19, each of the members 260 is disposed between respective members 270 and 270' and displaced towards the lumen 130 of the embolic device 100 in the radially expanded configuration, the members 260 have a smaller diameter $D_{12}$ than the diameter $D_{13}$ of members 270 and 270'.

In a further alternative embodiment, FIG. 20 comprises four evenly-spaced radio-opaque members 260 along the diameter $D_{20}$ composed of platinum, a first set of four evenly-spaced radio-opaque members 270 along the diameter $D_{20}$, and a second set of four evenly-spaced radio-opaque members 270' along the diameter $D_{20}$. The members 270 and 270' are composed of Nitinol. As shown in FIG. 20, each of the members 260 is disposed between respective members 270 and 270'. The members 207' are displaced towards the lumen 130 of the embolic device 100 in the radially expanded configuration, and the members 207 are displaced away from the lumen 130. Further, the members 260 have a smaller diameter $D_{21}$ than the diameter $D_{22}$ of members 270 and 270'. Particularly, FIG. 20 shows the cross-sectional view of the braided embolic device 100' of FIG. 9. Additionally, the elongated members of the braided embolic devices 100 of FIGS. 13-16 may comprise filaments, wires, drawn-filled tube or their like, composed of one or more suitable biocompatible materials, for example, nitinol and platinum drawn-filled tubes.

FIGS. 21A-26B illustrate further exemplary braided embolic devices comprising a variety of braid patterns portions, constructed according to the embodiments of the disclosed inventions. The embolic devices portions of FIGS. 21A-C and FIGS. 26A-B may comprise one or more of the braid patterns of the disclosed inventions, such as the patterns of FIGS. 2-7, or a combination of patterns thereof, or any other suitable braid pattern.

As shown in FIG. 21A, a braided embolic device 110 comprises an elongated configuration having a distal portion 122, a proximal portion 144, and a plurality of successive portions 180 extending therebetween. Similarly to the embolic device 100 of FIG. 8, the embolic device 110 has a radially compressed delivery configuration (not shown), and a radially expanded deployed configuration (shown in FIG. 21A), and preferably comprises a length that ranges from approximately 2 centimeters up to approximately 40 centimeters in the deployed configuration, and more preferably from approximately 5 centimeters up to approximately 25 centimeters in the deployed configuration. The embolic device 110 further comprises a plurality of elongate member 200 forming the braid 151 of the device 110, similarly to the embolic device 100. The plurality of portions 180 include alternating first portions 182 and second portions 184 of the embolic device 110 in the radially expanded deployed configuration. The first portions 182 of the embolic device 110 comprises a flat, ribbon-like configuration formed by a single layer of braid 151. Alternatively, the first portions 182 may be formed by more than one layer of braid 151, such as, a flattened tubular braid. The first portions 182 of the embolic device 110 comprising the ribbon-like configuration have rectangular cross-sections, as shown in FIG. 21B. Alternatively, the first portions 182 may have any other suitable cross-sections, for example: ovoid or elliptical, such as a tubular braid that is flattened, single-layer ribbon with rounded edges cross-section or the like, or combinations thereof. The second portions 184 of the embolic device 110 comprises a round or tube-like configuration formed by two or more of the plurality of elongate members 200 twisted, bundled, coupled together or the like. The two or more coupled elongate members 200 form an elongate set of members 200 between two of the first portions 182 of the embolic device 110. As shown in FIGS. 21A and 21C, the second portions 184 depicts elongate sets 200-1, 200-2, 2003, and 200-4 showing the tube-like configuration. Further, the round, tube-like configuration of the second portions 184 may be better appreciated in the cross-sectional view of FIG. 21C, further including elongated sets 200-5, and 200-6. By way of non-limited examples, each of the elongate sets 200-1 to 200-6 may be formed by having two elongate members 200 twisted together (FIG. 22), more than two elongate members 200 twisted together (FIG. 23), or by having the plurality of elongate members 200 bundled together (FIG. 24), or any other suitable coupling or combinations therefor (FIG. 25).

FIGS. 26A-B depict perspective side and top views of another embolic device 112, constructed according to the embodiments of the disclosed inventions. FIGS. 26A-B illustrate an embolic device 112 that is similar to the embolic device 110 depicted in FIGS. 21A-C. One difference is that the embolic device 112 comprises a braid 156 extending between the proximal portion 144' and distal portion 122' of the device 112 forming the plurality of successive portions 180'. Another difference is that the plurality of successive portions 180' further includes transition portions 183 between each of the first portions 182' and second portions 184' of the embolic device 110 in the radially expanded deployed configuration. Similarly to embolic device 110, the first portions 182' of the embolic device 112 comprises a flat, ribbon-like configuration and the second portions 184' of the embolic device 112 comprises a round or tube-like configuration. Further, the transition portions 183 may comprise tapered, cone-like configurations formed between the corresponding first 182' and second 184' portions of the embolic device 112, as shown in FIG. 26A. The braid 156 of the embolic device 112 may vary in pitch, i.e., a distance between respective elongate members 200, dimensions of the cells/openings, in pattern, and/or any other suitable configuration that allows for the formation of the plurality of successive portions 180'.

In the embodiments of FIG. 21A and FIGS. 26A-B, each of the first portions 182, 182' have respective length $L_1$ that are larger than the respective lengths $L_2$ of the second portions 184, 184'. The length $L_1$ of the first portions 182, 182' is approximately between 5 and 500 millimeters; preferably between 40 and 200 millimeters. The length $L_2$ of the second portions 184, 184' is approximately between 0.1 and 50 millimeters; preferably between 1 and 10 millimeters. The shorter length $L_2$ and/or the configuration of the second portions 184, 184' may form bending points that lower the axial and/or bending strength of the embolic devices 110, 112 at the corresponding second portions 184, 184' when a respective device 110, 112 is under compression. For example, during the delivery of the embolic device 110 from a delivery system into a target site in a patient (e.g., aneurysm sac), the device 110 would be subjected to axial and/or bending stress due to the force/pressure exerted by the advancing force and by the target site (e.g., aneurysm inner wall) that the device comes in contact with. As the result, the embolic device 110 bends or folds along the second portions 184 assuming a three dimensional configuration within the target site (e.g., aneurysm sac).

It should be appreciated that the embolic devices constructed according to the disclosed embodiments may be deployed at a target vascular site using devices and methods known in the art.

Although particular embodiments have been shown and described herein, it will be understood by those skilled in the art that they are not intended to limit the present inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. An implantable vaso-occlusive device for occluding an aneurysm, comprising:
   a braided member formed out of braid filaments, the braided member having compressed configuration when constrained in a lumen of a delivery catheter, and a tubular expanded configuration when not constrained, wherein when the braided member is in the expanded configuration, the braid filaments are disposed circumferentially about an elongate axis of the braided member,
   the braid filaments comprising a plurality of filaments made out of a first material, and one or more marker filaments made of a different material having a higher stiffness and a higher radiopacity, respectively, than the first material filaments;
   the marker filaments including a plurality of sets of adjacent marker filaments, wherein each set of adjacent marker filaments is circumferentially offset from the other sets, and each set of adjacent marker filaments includes a first marker filament made out of a different material and having a different diameter or cross-section, respectively, than a second marker filament of the respective set of adjacent marker filaments; and
   within each set of adjacent marker filaments, the first marker filament is positioned at a different radial distance from a longitudinal axis of the braided member than a radial distance of the second marker filament.

2. The vaso-occlusive device of claim 1, wherein the first material filaments are made out of nickel-titanium alloy, the first marker filaments are made out of platinum alloy and the second marker filaments are made out of a radiopaque material.

3. The vaso-occlusive device of claim 1, wherein the marker filaments include first and second marker filaments that are circumferentially offset approximately 180° from each other along at least a portion of the braided member when the braided member is in the tubular expanded configuration.

4. The vaso-occlusive device of claim 3, wherein the second marker filaments are made out of nitinol and platinum drawn-filled tubes.

5. The vaso-occlusive device of claim 1, wherein the marker filaments include four sets of adjacent marker filaments that are circumferentially offset approximately 90° from each other along at least a portion of the braided member when the braided member is in the tubular expanded configuration.

6. The vaso-occlusive device of claim 5, wherein the first material filaments are made out of nickel-titanium alloy, the first marker filaments are made out of platinum alloy and the second marker filaments are made out of nitinol.

7. The vaso-occlusive device of claim 1, wherein the marker filaments include six sets of adjacent marker that are circumferentially offset approximately 60° from each other along at least a portion of the braided member when the braided member is in the tubular expanded configuration.

8. The vaso-occlusive device of claim 1, wherein the marker filaments include two sets of adjacent marker filaments that are circumferentially offset approximately 180° from each other along at least a portion of the braided member when the braided member is in the tubular expanded configuration.

9. The vaso-occlusive device of claim 8, wherein the first material filaments are made out of nickel-titanium alloy, the first marker filaments are made out of platinum alloy and the second marker filaments are made out of nitinol.

10. The vaso-occlusive device of claim 9, wherein the second marker filaments are made out of nitinol and platinum drawn-filled tubes.

11. The vaso-occlusive device of claim 8, wherein each set of adjacent marker filaments comprises first, second and third marker filaments disposed adjacent each other, wherein the first marker filament is made out of a different material and has a different diameter or cross-section, respectively, than one or both of the second and third marker filaments.

\* \* \* \* \*